United States Patent [19]

Groner

[11] Patent Number: 4,989,978
[45] Date of Patent: Feb. 5, 1991

[54] METHOD AND APPARATUS FOR DETERMINING THE COUNT PER UNIT VOLUME OF PARTICLES

[75] Inventor: Warren Groner, Whitestone, N.Y.

[73] Assignee: Technicon Instruments Corporation, Tarrytown, N.Y.

[21] Appl. No.: 848,172

[22] Filed: Apr. 4, 1986

[51] Int. Cl.⁵ ............................................. G01N 21/53
[52] U.S. Cl. ....................................... 356/343; 356/39
[58] Field of Search .................... 356/336, 338, 343, 39

[56] References Cited

U.S. PATENT DOCUMENTS

| | | | |
|---|---|---|---|
| 3,549,994 | 12/1970 | Rothermal et al. | 356/39 |
| 3,740,143 | 6/1973 | Groner et al. | 356/39 |
| 4,429,995 | 2/1984 | Goulas | 356/393 |
| 4,548,500 | 10/1985 | Wyatt et al. | 356/336 |
| 4,577,964 | 3/1986 | Hansen, Jr. | 356/343 |
| 4,735,504 | 4/1988 | Tycko | 356/336 |

FOREIGN PATENT DOCUMENTS 0008874  5/1982  European Pat. Off. .
3341749  2/1984  Fed. Rep. of Germany .

OTHER PUBLICATIONS

Tycko et al., "Flow-Cytometric Light Scattering Measurement of Red Blood Cell Volume and Hemoglobin Concentration" *Applied Optics.*, vol. 24, No. 9, May 1985, pp. 1355-1365.

*Primary Examiner*—Richard A. Rosenberger
*Attorney, Agent, or Firm*—Scully, Scott, Murphy & Presser

[57] ABSTRACT

A method and apparatus for accurately determining the count per unit volume of particles, such as red blood cells, suspended in a fluid containing at least one undesirable interference particle, such as air bubbles. A predetermined volume of fluid containing the first and second particles is passed through the a flow cytometer which produces a forward light scattering pattern that is detected and measured. The volume and index refraction of each of the first and second particles is determined. The first and second particles are discriminated in accordance with their respective indices of refraction and the total count and volume of particles is corrected to provide the count per unit volume of red blood cells.

24 Claims, 3 Drawing Sheets

METHOD AND APPARATUS FOR DETERMINING THE COUNT PER UNIT VOLUME OF PARTICLES

BACKGROUND OF THE INVENTION

1. Field of the Invention

This invention is directed to a method and apparatus for accurately determining the count per unit volume of particles suspended in a fluid containing one or more undesirable particles. More particularly, the invention pertains to determining the count per unit volume of blood cells in a flow cytometric system wherein the count is corrected for air bubbles present in the blood suspension medium.

2. Description of the Prior Art

The use of flow cytometry for counting blood cells has been increasing over the past several years. A fundamental consideration in the accuracy of blood cell counting is that the suspension of blood cells, if allowed to sit unmixed, will become spatially inhomogeneous due to sedimentation or sticking to the container walls. This occurs due to the fact that the blood cells are in general denser than the fluid they are suspended in and may also have an electrostatic interaction with the walls of the container. This inhomogeniety may interfere with the accuracy of the blood cell counting.

In order to solve this problem, the suspension of blood cells is mixed prior to the cells being passed through the counting mechanism. However, if the suspension is mixed, air bubbles will be introduced into the fluid which may interfere with the accuracy of the blood cell count. This interference is generally caused by the trapped air increasing the fluid volume measured by the system which erroneously lowers the cell count and also by small air bubbles which may be counted as cells erroneously increasing the cell count.

Heretofore, there has not been a system for solving the substantial problems in counting blood cells in a flow cytometer. At present, if the suspension is sampled during or shortly after mixing, error due to air is introduced and if counting is delayed to remove the air, cell loss due to sedimentation or sticking to the container walls is observed.

SUMMARY OF THE INVENTION

The present invention is directed to a method and apparatus for accurately determining the count per unit volume of particles that overcomes the sources of potential error in a system utilizing flow cytometric techniques. The invention discriminates between undesirable particles and desired particles on the basis of a difference in relative index of refraction. The count of desired particles is then corrected to take into account the undesirable particles to provide an accurate count per unit volume.

The particles desired to be counted, such as red blood cells, are suspended in a fluid. The suspension fluid may contain one or more air bubbles that become introduced as a result of mixing of the fluid. The red blood cells have an index of refraction different from the index of refraction of the air bubbles. A predetermined volume of fluid containing both cells and air bubbles is aspirated from a mixing chamber and each particle, in turn, is passed through a light beam. Each particle produces at least one forward light scattering pattern. This forward light scattering pattern is described in the commonly assigned patent application entitled Method for Simultaneous Measuring of RBC Volume and Hemoglobin Concentration, Ser. No. 547,513 the entire specification of which is herein incorporated by reference. The above-mentioned application utilizes a multiple angle light scattering measurement technique from which there can be determined the volume and index of refraction of particles passing through a flow cytometer.

The intensity of light from at least a portion of the scattering pattern is detected and measured and a signal representative of such intensity is generated. All the particles in the aspirated volume of fluid are passed through the light beam and the combined total number of particles is counted. The volume and index of refraction of each of the particles is thereafter determined using the multiple angle technique. A discriminator separates the cells and air bubbles by their respective indices of refraction. Thereafter, the count and volume of particles is corrected by the count and volume of air bubbles to determine the count per unit volume of red blood cells.

The intensity of light from the scattering pattern is detected within a plurality of angular intervals and a signal is generated from each angular interval. The angular intervals are uniquely selected such that the light contains sufficient information to determine the volume and index of refraction of the particles. As disclosed in copending application Ser. No. 547,513, it is preferred that two angular intervals be selected. A two-dimensional graphical representation may be provided which shows a first region of particles having the index of refraction of blood cells and second region of particles having the index of refraction of air.

In one embodiment, a threshold technique is utilized to separate the blood cells from air. A threshold value is set in accordance with the indices of refraction of the blood cells and air so that only those particles above or below the threshold are counted. Since the number of cells will be much more than the number of air bubbles, only the number and volume of air bubbles are determined and then the total count initially measured and detected can be corrected for the amount of air to provide an accurate count per unit volume of red blood cells.

DETAILED DESCRIPTION OF THE INVENTION

Figure 1:
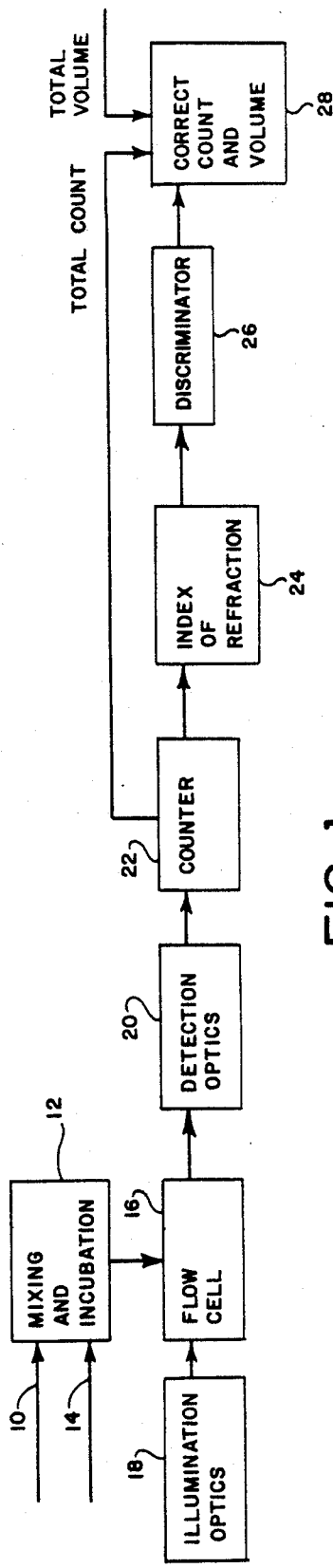
FIG. 1 is a block diagram of a preferred embodiment of the present invention.

Referring now to the drawings, FIG. 1 shows a block diagram of the system of the present invention wherein blood cells are introduced through conduit 10 into a mixing and incubation chamber 12. The conduit 10 comprises a conventional sampling apparatus, not shown, for introducing blood cells into the chamber 12. A suspension fluid is introduced through conduit 14 to suspend the cells therein. An isovolumetric sphering reagent may also be introduced along conduit 14 to sphere the red blood cells contained in the sample. The isovolumetric sphering of the red blood cells ensures that the measurement is fully independent of the orientation of the cell during optical measurement in a flow cytometer.

The individual cells are first mixed in the chamber 12 to mix with the suspension fluid and to react with the sphering agent. The cells are then permitted to incubate during which a number of cells may stick to the chamber walls and/or settle on the chamber bottom. The sedimentation will occur as mentioned, due to the blood cells being denser than the suspension fluid. In addition, the cells may have an electrostatic interaction with the walls of the container 12 thereby causing them to be attracted to the walls. Thus, if allowed to sit unmixed prior to passage through the flow cytometer, the cells will become spatially inhomogenous which will interfere with the accuracy of the blood count. Following incubation, the cells are again mixed in the chamber 12 prior to being passed to a flow cell 16 in order to avoid the problem of spatial inhomogeneity. As noted previously, mixing generally will cause a plurality of air bubbles to be formed in the suspension fluid.

Figure 2:
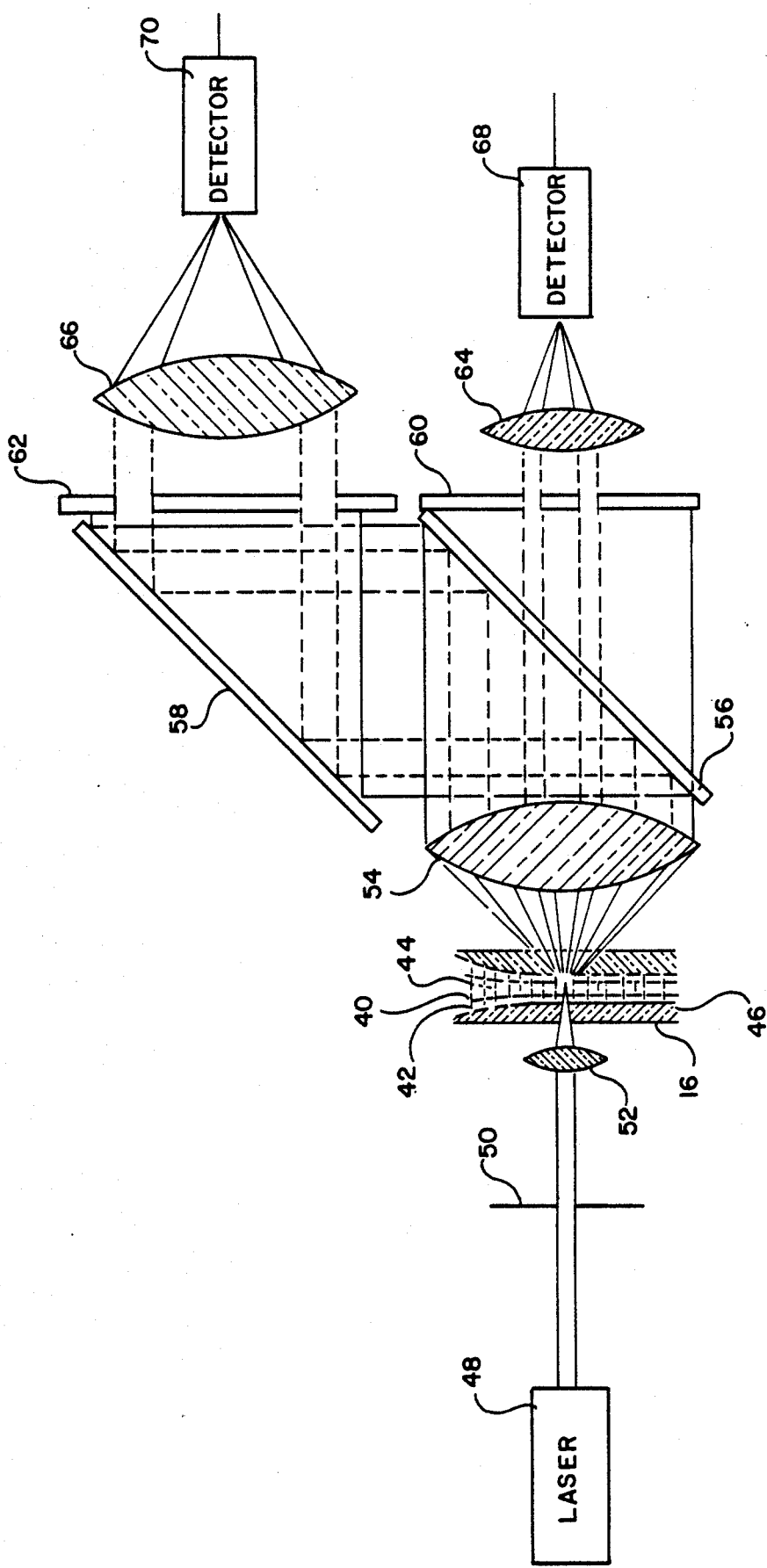
FIG. 2 is a schematic diagram of the flow cell and detection optics used in the present invention.

In accordance with the inventive method, a predetermined volume of suspension fluid having cells and air bubbles is aspirated from the mixing chamber 12. Therefore, each cell is passed through the flow cell 16 for detection. In addition, any air bubbles in the aspirated volume will also be detected. A conventional aspirating device, not shown, may be used to pass the predetermined volume of fluid from the mixing chamber 12 to the flow cell 16. The flow cell 16 can be of conventional design, for example, as described in U.S. Pat. No. 3,661,460, assigned to a common assignee which discloses a sheath-stream flow cell. As shown in FIG. 2, the fluid stream 40 is passed through the flow cell 16 which is designed so that individual cells flow successively through an optically defined view volume. The stream 40 is encased in a sheath 42 having an index of refraction the same as the stream 40. The red blood cells 44 flow through the passageway 46 which has a narrowing internal diameter thereby constricting the stream 40 to cause individual cells to flow through the view volume.

Illumination optics 18 directs a light beam through the view volume to illuminate, in turn, each particle as it passes through the cell 16. The illumination comprises a laser 48, precision slit aperture 50 and a lens system 52 for condensing the light beam into the center of the view volume, as shown in FIG. 2 while maintaining the substantially collimated light from the laser 48.

As each individual particle passes, in turn, through the view volume of flow cell 16, it interrupts the light beam. Accordingly, light is scattered mainly in the forward direction and in an angular intensity pattern from which the volume and index of refraction can be measured. The intensity of light in the scattering pattern is detected and measured in the detection optics 20 which generates an electrical signal. The signal is then processed to determine the desired information as will be hereinafter described. The detection optics utilizes the multiple angle light scattering measurement technique described in detail in commonly assigned, copending U.S. application Ser. No. 547,513. Briefly, as shown in FIG. 2, the detection optics includes a lens 54 which collects the forward scattered light within two critical angular intervals which are separately detected and measured from which the volume and index of refraction of each individual particle is determined. The light from the lens is directed to a beam splitter 56 which transmits approximately half the light and reflects the remaining light which is directed to and reflected from a mirror 58. The light passed through the beam splitter 56 is directed through a dark field stop 60 adapted to pass light scattered within a low angular interval. Similarly, light reflected from mirror 58 is directed through a dark field stop 62 adapted to pass light scattered within a high angular interval. The light from the two different angles is collected by lenses 64 and 66 and then detected by two separate detectors 68 and 70 respectively.

Returning now to FIG. 1, a counter 22 counts the combined total of particles passing through the flow cell 16. The signal is then transmitted to index of refraction processor 24 where the volume and index of refraction of each particle is determined. The processor 24 utilizes the technique disclosed in pending U.S. application Ser. No. 547,513 to process the detected signals to determine the volume and index of refraction of each particle.

Figure 3:
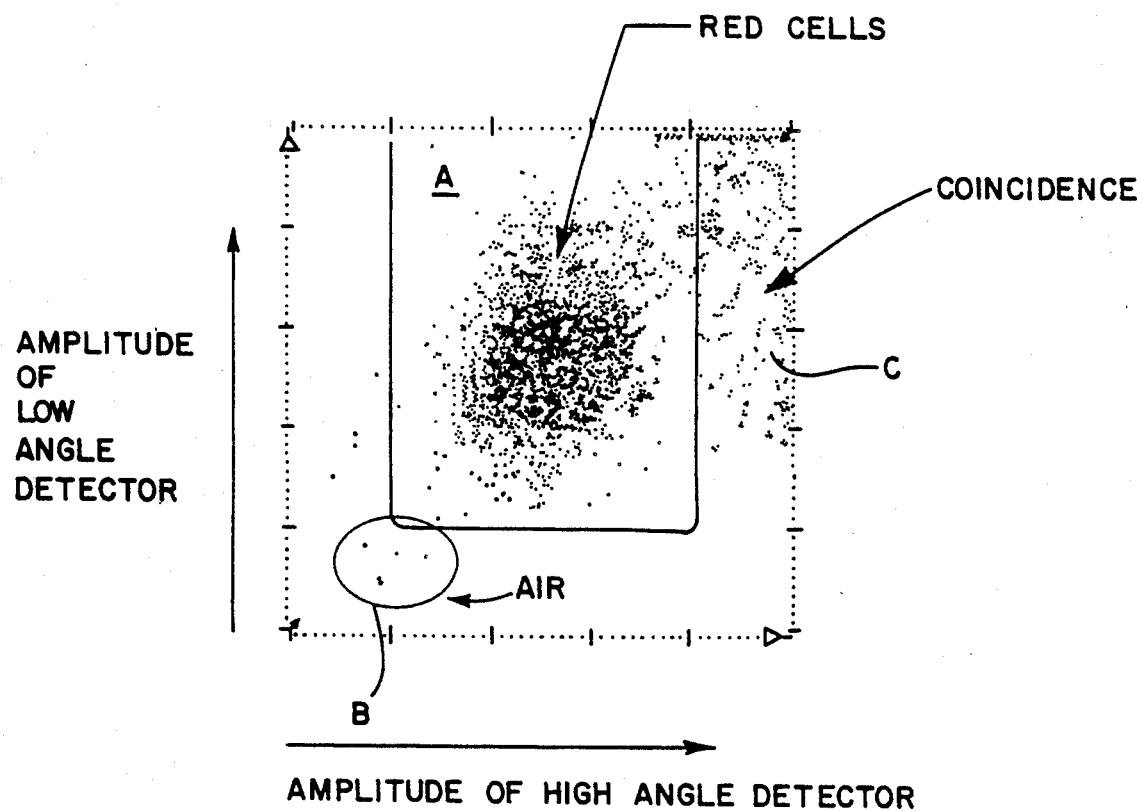
FIG. 3 is a graphical representation of the separation of particles by their indices of refraction.

A discriminator 26 distinguishes between the blood cells and air bubbles by their respective indices of refraction. The index of refraction of air is approximately 1.00, while the index of refraction of red blood cells is approximately in the range of 1.38 to 1.44. The discriminator 26 separates the signals in accordance with the measured index of refraction. A graphical representation may be obtained by plotting the results for each particle. The graph will depict one region of the particles having one index of refraction and a second region of particles having a second index of refraction. An example of such a graph is shown in FIG. 3. Region A includes the concentration of red blood cells while region B includes the air bubbles. Region C shows the effect of occasional coincidence of red cells in the view volume. Errors due to coincidence may be corrected by standard techniques commonly used in cell counters.

Thereafter, processor 28 is utilized to correct the count and volume for the detected air bubbles to provide an accurate determination of the count per unit volume of red blood cells. The total count of particles passed through the flow cell is inputted to the processor 28 together with the predetermined volume of fluid aspirated. Processor 28 is programmed with an algorithm that will take the total number of particles counted and subtract the number of air bubbles to provide an accurate count of red blood cells. In addition, processor 28 will subtract the volume of air bubbles from the total volume of particles aspirated to determine the accurate volume of red blood cells. The number of cells is then divided by the volume of cells to provide an accurate measurement of the total count per unit volume of red blood cells.

Moreover, the processor 28 can be a microprocessor programmed with an algorithm that sets a threshold value at either of the measured indices of refraction. Processor 28 can include a counter to count only those particles above or below the threshold value. An adder will then determine the total volume of particles counted. In addition, the mean volume per air bubbles can be calculated and multiplied by the number of air bubbles to determine the total volume of air in the sample stream.

Figure 4:
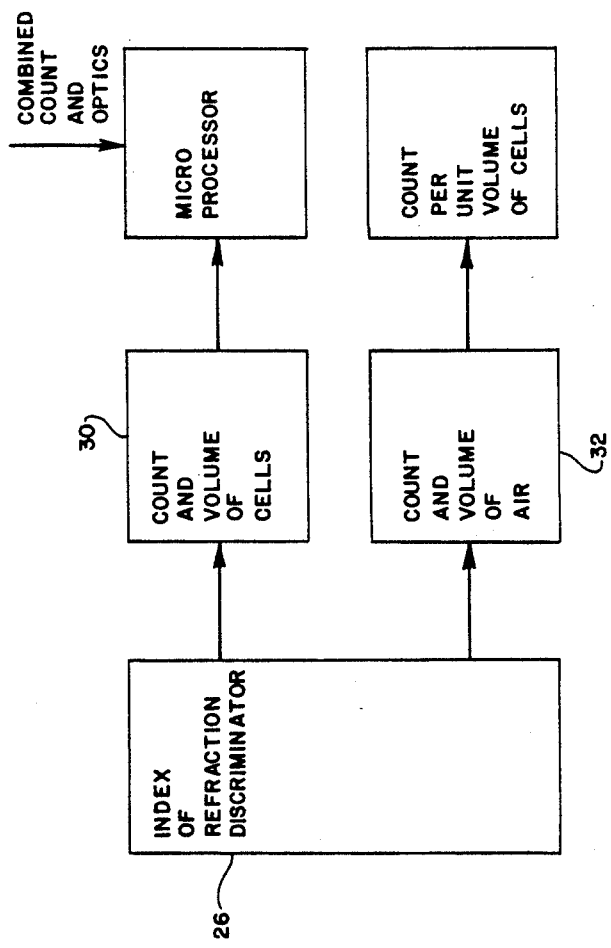
FIG. 4 is a block diagram showing separate counters between the discriminator and the microprocessor.

FIG. 4 illustrates the use of separate counting means 30 and 32 coupled between the discriminator 26 and processor 28. After discriminator 26 separates signals in accordance with the indices of refraction, counters 30 and 32 then individually count each of the signals in the two regions. This information is fed to the processor 28 together with the combined count and volume originally measured and detected to determine the accurate count per unit volume of blood cells.

While illustrative embodiments of the subject invention have been described and illustrated, it is obvious that various changes and modifications can be made therein without seperating from the spirit of the present invention which should be limited only by the scope of the appended claims.

What is claimed is:

1. A method for accurately determining the count per unit volume of first particles suspended in a fluid containing said first particles having a first index of refraction and at least one second particle having a second index of refraction different from the first index of refraction, comprising the steps of:
passing each of said first and second particles from a predetermined volume of suspension fluid, in turn, through a light beam, each of said first and second particles producing, at least one forward light scattering pattern;
detecting and counting the combined total number of said first and second particles passing through said light beam from said light scattering pattern;
measuring the index of refraction of said second particles above or below a threshold value and counting and determining the volume of said second particles; and
correcting the total count and volume of particles by the count and volume of said second particles to determine the count per unit volume of said first particles.

2. The method of claim 1, wherein the combined total number of said first and second particles is detected by measuring the intensity of light of at least a portion of each of said light scattering patterns.

3. The method of claim 2 further including the steps of:
determining the volume and index of refraction of each of said first and second particles passing through said light beam from said at least one forward light scattering pattern; and
discriminating between said first and second particles by their respective first and second indices of refraction.

4. The method of claim 1, wherein the correcting step includes the steps of:
determining the total number and volume of said second particles;
determining the count and volume of said first particles passing through said light beam by modifying the combined total count of particles and the predetermined volume of fluid with the number and volume of second particles; and
determining the count per unit volume of said first particles from the modified count and volume thereof.

5. The method of claim 4, wherein said first particles are red blood cells and said second particles are air bubbles.

6. The method of claim 5, further including the step of aspirating a volume of said fluid from a mixing chamber prior to passing the fluid through the light beam.

7. The method of claim 6, further including the step of mixing the fluid containing red blood cells causing air bubbles to be formed in said fluid prior to aspiration.

8. The method of claim 1, wherein the step of determining the volume and index of refraction of each of said first and second particles includes the steps of:
detecting and measuring the intensity of light within each of a plurality of angular intervals of said scattering pattern to generate a signal from each angular interval, wherein said angular intervals are selected such that the light contained therein contains sufficient information for the precise determination of the volume and index of refraction of said first and second particles; and
determining the volume and index of refraction of said first and second particles from the magnitudes of said signals.

9. A method for accurately determining the count per unit volume of blood cells having a first index of refraction suspended in a fluid containing a plurality of air bubbles having a second index of refraction different from the first index of refraction, comprising the steps of:
aspirating a predetermined volume of said fluid containing said blood cells and air bubbles from a mixing chamber;
passing each of said blood cells and air bubbles, in turn, through a beam of light, each of said blood cells and air bubbles producing at least one forward light scattering pattern;
counting the combined total number of blood cells and air bubbles passing through said light beam;
determining the volume and index of refraction of each of said blood cells and air bubbles passing through said light beam from said at least one forward light scattering pattern;
discriminating between said blood cells and air bubbles by their respective first and second indices of refraction;
determining the total number and volume of said air bubbles;
determining the count and volume of said blood cells passing through said light beam by modifying the combined total of cells and bubbles and the predetermined volume of fluid with the number and volume of air bubbles; and
determining the count per unit volume of said blood cells from the modified count and volume thereof.

10. The method of claim 1 or 9, wherein the discriminating step includes the step of providing a two-dimensional graphical representation depicting a first region of particles having said first index of refraction and a second region of particles having said second index of refraction.

11. The method of claim 10, wherein the discriminating step includes setting a threshold at either of said first or second index of refraction and counting only those particles above or below said threshold.

12. The method of claim 11, further including the step of calculating the mean volume per second particle and multiplying said mean volume by the number of said second particles to determine the total volume of said second particles.

13. The method of claim 12, wherein the count per unit volume of first particles is determined by dividing the count of first particles by the volume of predetermined fluid less the volume of second particles.

14. An apparatus for accurately determining the count per unit volume of first particles suspended in a fluid containing said first particles having a first index of refraction and at least one second particle having a second index of refraction different from the first index of refraction comprising the steps of:

means for passing each of said first and second particles from a predetermined volume of suspension fluid in turn, through a light beam, each of said first and second particles producing at least one forward light scattering pattern;

means for detecting and counting the combined total number of said first and second particles passing through said light beam from said light scattering pattern;

means for measuring the index of said second particles above or below a threshold value and counting and determining the value of said second particles; and means for correcting the total count and volume of particles by the count and volume of said second particles to determine the count per unit volume of said first particles.

15. The apparatus of claim 14, wherein the means for detecting the combined total number of said first and second particles includes means for measuring the intensity of light of at least a portion of each of said light scattering patterns.

16. The apparatus of claim 15 further including:

means for determining the volume and index of refraction of each of said first and second particles passing through said light beam from said at least one forward light scattering pattern; and means for discriminating between said first and second particles by their respective first and second indices of refraction.

17. The apparatus of claim 14 wherein the correcting means includes:

means for determining the total number and volume of said second particles;

means for determining the count and volume of said first particles passing through said light beam by modifying the combined total of particles and the predetermined volume of fluid with the number and volume of second particles; and means for determining the count per unit volume of said first particles from the modified count and volume of said first particles.

18. The apparatus of claim 14 further including means for aspirating a predetermined volume of fluid from a mixing chamber.

19. The apparatus of claim 18 wherein the first particles are blood cells and the second particles are air bubbles and further including means for mixing the fluid containing blood cells causing air bubbles to be formed in said fluid.

20. The apparatus of claim 14 wherein said discriminating means includes a means for providing a two dimensional graphical representation showing a first region of particles having said first index of refraction and a second region of particles having said second index of refraction.

21. The apparatus of claim 14 wherein said correcting means includes counter means for counting those particles above and below a threshold index of refraction and an adding means for determining the total volume of particles counted by said counting means.

22. The apparatus of claim 14 further including a microprocessor for calculating the mean volume per second particles to determine the total volume of said second particles and calculating the count per unit volume of said first particles.

23. The apparatus of claim 14 wherein said volume and index of refraction determining means includes:

means for detecting and measuring the intensity of light within each of a plurality of angular intervals of said scattering pattern and for generating a signal from each angular interval wherein said angular intervals are selected such that the light contained therein contains sufficient information for the precise determination of the volume and index of refraction of said particle; and means responsive to said detecting and measuring means for determining the volume and index of refraction of said particle from the magnitudes of said signals.

24. An apparatus for accurately determining the count per unit volume of blood cells having a first index of refraction suspended in a fluid containing a plurality of air bubbles having a second index of refraction different from the first index of refraction, comprising the steps of:

means for aspirating a predetermined volume of said fluid containing said blood cells and air bubbles from a mixing chamber;

means for passing each of said blood cells and air bubbles, in turn, through a beam of light, each of said blood cells and air bubbles, producing at least one forward light scattering pattern;

means for detecting and measuring the intensity of light of at least a portion of said light scattering pattern to generate a signal;

means for counting the combined total number of blood cells and air bubbles passing through said light beam;

means for determining the volume and index of refraction of each of said blood cells and air bubbles passing through said light beam from said at least one forward light scattering pattern;

means for discriminating between said blood cells and air bubbles by their respective first and second indices of refraction;

means for determining the total number and volume of said air bubbles;

means for determining the count and volume of said blood cells passing through said light beam by modifying the combined total of cells and bubbles and the predetermined volume of fluid with the number and volume of air bubbles; and means for determining the count per unit volume of blood cells from the modified count and volume thereof.

* * * * *